United States Patent
Voorhees et al.

(10) Patent No.: US 7,268,148 B2
(45) Date of Patent: Sep. 11, 2007

(54) COMPOSITIONS AND METHODS FOR USE AGAINST ACNE-INDUCED INFLAMMATION AND DERMAL MATRIX-DEGRADING ENZYMES

(75) Inventors: John J. Voorhees, Ann Arbor, MI (US); Gary J. Fisher, Ypsilanti, MI (US); Sewon Kang, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/169,072

(22) Filed: Jun. 27, 2005

(65) Prior Publication Data

US 2005/0277695 A1    Dec. 15, 2005

Related U.S. Application Data

(63) Continuation of application No. 09/576,597, filed on May 22, 2000, now abandoned.

(60) Provisional application No. 60/134,984, filed on May 20, 1999.

(51) Int. Cl.
*A61K 31/445* (2006.01)
*A61K 31/443* (2006.01)
*A61K 31/38* (2006.01)

(52) U.S. Cl. ............ 514/311; 514/312; 514/314; 514/443; 514/437; 514/454

(58) Field of Classification Search ......... 514/311, 514/312, 314, 443, 437, 454; 549/16, 26, 549/43; 435/7.1
See application file for complete search history.

(56) References Cited

U.S. PATENT DOCUMENTS

| | | | | |
|---|---|---|---|---|
| 4,942,031 A | * | 7/1990 | Levin | 424/520 |
| 5,292,512 A | * | 3/1994 | Schaefer et al. | 424/401 |
| 5,411,742 A | * | 5/1995 | Sebag et al. | 424/450 |
| 5,460,620 A | * | 10/1995 | Smith et al. | 604/290 |
| 5,605,894 A | * | 2/1997 | Blank et al. | 514/159 |
| 5,607,921 A | * | 3/1997 | Bernard et al. | 514/23 |
| 5,728,846 A | * | 3/1998 | Vuligonda et al. | 549/16 |
| 5,739,338 A | * | 4/1998 | Beard et al. | 546/153 |
| 5,834,044 A | * | 11/1998 | Schmitz et al. | 426/73 |
| 5,952,373 A | * | 9/1999 | Lanzendorfer et al. | 514/456 |
| 5,972,999 A | * | 10/1999 | Murad | 514/474 |
| 6,051,731 A | * | 4/2000 | Vuligonda et al. | 560/56 |
| 6,218,128 B1 | * | 4/2001 | Klein et al. | 435/7.1 |
| 6,294,546 B1 | * | 9/2001 | Rosen et al. | 514/280 |
| 6,306,879 B1 | * | 10/2001 | Germann et al. | 514/323 |

* cited by examiner

*Primary Examiner*—Vickie Kim
(74) *Attorney, Agent, or Firm*—Bradley N. Ruben

(57) ABSTRACT

Acne-affected skin has been found to be accompanied by the presence of matrix-degrading enzymes such as MMPs and neutrophil elastase, induction of neutrophils, and a reduction in procollagen biosynthesis. This invention treats scarring and inflammation accompanying acne by administering, topically or systemically, at least one of (i) an inhibitor of the matrix degrading enzymes and (ii) a cytokine inhibitor that alleviates inflammation and thus also alleviate neutrophil infiltration. Alleviating the matrix degradation and renormalizing procollagen biosynthesis allows for reduced inflammation and better natural repair of acne-affected skin. Inhibiting cytokines alleviates induction of MMPs in resident skin cells, and also alleviates inflammation with its concomitant induction of neutrophils from the blood stream bringing MMPs and elastase into the acne lesion. Dimishing the presence of matrix-degrading enzymes in the acne lesion reduces imperfect repair of the skin and thus decreases scarring in acne-affected skin.

14 Claims, 7 Drawing Sheets
(5 of 7 Drawing Sheet(s) Filed in Color)

Fig. 1

MMP-8 IS ELEVATED IN ACNE LESIONS (L), AS COMPARED WITH UNINVOLVED ADJACENT SKIN (C) AND IS REDUCED BY TOPICAL RA (0.1%)

Fig. 7A
No Treatment
Uninvolved

Fig. 7B
No Treatment
Involved

COMPOSITIONS AND METHODS FOR USE AGAINST ACNE-INDUCED INFLAMMATION AND DERMAL MATRIX-DEGRADING ENZYMES

This application is a continuation of Ser. No. 09/576,597, filed May 22, 2000, now abandoned, which is based on provisional application 60/134,984, filed May 20, 1999, the disclosures of which are incorporated herein by reference.

TECHNICAL FIELD

This invention involves protecting human skin from some of the effects of acne, especially acne vulgaris, through the use of the topically and/or systemically applied non-retinoid and non-steriod compounds that diminish inflammation and matrix-degrading enzymes in acne-affected skin.

BACKGROUND

Acne is a multifactorial disease, developing in the sebaceous follicles. At least one agent thought responsible is the anaerobe *Propionibacterium acnes* (*P. acnes*); in younger individuals, practically no *P. acnes* is found in the follicles of those without acne.

The disease of acne is characterized by a great variety of clinical lesions. Although one type of lesion may be predominant (typically the comedo), close observation usually reveals the presence of several types of lesions (comedones, pustules, papules, and/or nodules). The lesions can be either noninflammatory or, more typically, inflammatory. In addition to lesions, patients may have, as the result of lesions, scars of varying size. The fully developed, open comedo (i.e., a plug of dried sebum in a skin pore) is not usually the site of inflammatory changes, unless it is traumatized by the patient. The developing microcomedo and the closed comedo are the major sites for the development of inflammatory lesions. Because the skin is always trying to repair itself, sheaths of cells will grow out from the epidermis (forming appendageal structures) in an attempt to encapsulate the inflammatory reaction. This encapsulation is often incomplete and further rupture of the lesion typically occurs, leading to multichanneled tracts as can be seen in many acne scars.

In general, there are four major principles presently governing the therapy of acne: (i) correction of the altered pattern of follicular keratinization; (ii) decrease sebaceous gland activity; (iii) decrease the follicular bacterial population (especially *P. acnes*) and inhibit the production of extracellular inflammatory products through the inhibition of these microorganisms; and (iv) produce an anti-inflammatory effect. The present treatments for acne following these principals typically include: vitamin A acid (retinoic acid), known for its comedolytic properties, administered topically (e.g., Retin-A® brand 0.025% all-trans retinoic acid cream) or systemically (e.g., Accutane® brand 13-cis retinoic acid); an antibiotic administered systemically (e.g., tetracycline or one of its derivatives) or topically (e.g., benzoyl peroxide, erythromycin, clindamycin, azelaic acid); the use of other comedolytic agents such as salicylic acid; or the use of systemic anti-androgens such as cyproterone acetate and spironolactone (because androgens promote sebum production, and sebum has been found to be comedogenic and inflammatory), which may be administered in combination with an estrogen. Atrophy, the most feared side effect of topical glucocorticoids, is seen as an overall reduction in the dermal volume and occurs as early as one week after superpotent-steroid use. Systemic side effects of chronic glucocorticoid use include suppression of the hypothalamic-pituitary-adrenal (HPA) axis, Cushing's syndrome, glaucoma, and, in children, failure to thrive. (Children, especially infants and young children, are at higher risk for systemic side effects due to their greater surface-to-body ratio. They also may not metabolize corticosteroids as well as adults.) Withdrawal symptoms can appear after topical steriods have been used for a long period of time. Severe flaring may occur when isotretinoin (13-cis) therapy is started, and so concommitant use of a steriod, and suboptimal doses of isotretinoin, are often required at the start of therapy; additionally, retinoids generally are teratogenic (inhibiting organogenesis as opposed to being mutagenic).

The art has addressed inflammation and scarring caused by acne as a secondary benefit to the treatment of the disease; that is, if the acne is cured the factors causing scarring will be eliminated. There is otherwise no treatment directed at preventing scarring from acne. Neither is there presently any direct treatment for the inflammation accompanying acne. The conventional treatment acts to prevent further problems by alleviating the cause of the acne; for example, a patient is treated with tetracycline, an antiobiotic, in hopes of killing the *P. acnes*, and the death of the bacteria will effectively end the inflammation and future scarring. Much as antipyretics, analgesics, decongestants, and antihistamines have been developed to treat the symptoms of colds and upper respiratory infections (as opposed to antibiotics and antivirals to kill off the invading bacteria and viruses), there is a need for treatments diminishing if not preventing scarring and inflammation in acne.

SUMMARY OF THE INVENTION

One object of this invention is to reduce and/or eliminate scarring in acne-affected skin.

Another object of this invention is to reduce and/or eliminate the inflammatory reaction that accompanies acne.

We have discovered that acne lesions are not only inflammatory, but that enzymes that degrade the dermal matrix, including metalloproteinases (MMPs) and other proteases such as neutrophil elastase, are present in the lesion, and these enzymes likely cause, or at least significantly contribute, to scarring. Additionally, the *P. acnes* products from the lesion are believed to initiate a signalling cascade which both induces these degradatory enzymes within the skin and also induces PMNs (polymorphic leukocytes; e.g., neutrophils) to migrate to the lesion and contribute to the induction of degradatory enzymes. Still further, the *P. acnes* products are believed to cause a signalling cascade leading to inflammation.

Our invention is the treatment and prevention of scarring caused by acne, which treatment and prevention is accomplished through the administration of a composition comprising an effective amount of an non-retinoid, non-glucocorticoid inhibitor of a dermal matrix-degrading enzyme to acne-affected skin. Adminstration may be topical, systemic (preferably oral), or a combination thereof, and may be given in combination with another, conventional acne therapy (e.g., benzoyl peroxide, a retinoid, or a tetracycline). In yet another embodiment, the topical application of a dermal matrix-degrading enzyme inhibitor includes the administration of inhibitors of both MMPs and other proteases. The inhibitor can be a direct inhibitor, acting specifically on the enzyme, or an indirect inhibitor, tying up a signalling compound in a pathway leading to the matrix-degrading enzyme.

Another aspect of the invention is the administration of a compound that inhibits the inflammatory reaction and/or the recruitment of cells resulting in an inflammatory reaction in the acne lesion. Likewise, this administration can be topical, systemic (e.g., oral), or a combination thereof. Similarly, this administration can be accompanied by the co-administration of a conventional acne therapy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

The matrix of the skin (the dermal matrix), a structural framework that supports the cells and other structures in the skin, is comprised of collagen and elastin proteins for structural and dynamic (elastic) support.

Scarring of acne-affected skin has been known for a long time, and the typical treatment philosophy is that curing the acne will eliminate future scarring. As described in the Background section, it has also been known that acne includes bacterial infestation and an inflammatory reaction.

We have discovered that neutrophils (PMNs), immune cells that migrate to areas of injury, invade acne-affected skin, and release both a collagenase (MMP-8) and another protease (neutrophil elastase) that likely exacerbate scarring. Additionally, we have discovered that acne-affected skin has an elevated collagenase (MMP-1) level from resident skin cells that further exacerbates scarring. By inhibiting these dermal matrix-degrading enzymes, scarring of acne-affected skin can be lessened. Neutrophils circulate in the blood and therfore must be recruited by a signalling mechanism to induce their presence in the skin, facilitate their infiltration to the affected site, and enable their release of MMP-8 and elastase. Accordingly, impeding or disrupting the signalling which induces their presence in the skin and/or the activity of MMP-8 or elastase is likely to diminish the accompanying inflammation and the degradatory action of MMP-8 and/or elastase.

Matrix metalloproteinases (MMPs) are a family of enzymes that play a major role in physiological and pathological destruction of connective tissue, especially collagen. Various types of collagen and collagenases (types of MMPs) are known in this field, and a further description can be found in U.S. Pat. No. 5,837,224, and in our co-pending application 89,914, filed 3 Jun. 1998, the disclosures of which are incorporated herein by reference in their entirety for all purposes. Inhibitors of MMPs (e.g., direct inhibitors of the proteinase) and of molecular pathways (e.g., inhibitors of AP-1 and/or NF-κB) that affect MMP expression are known in other fields and likewise are described in U.S. Pat. No. 5,837,224 and the 89,914 co-pending application.

MMP-8 preferentially degrades Type I collagen and is a more active enzyme than MMP-1 and so degrades collagen better. Neutrophils also release an elastase, a serine protease, an enzyme that degrades elastin protein in the dermal matrix.

This invention inhibits scar formation in acne-affected skin by inhibiting MMPs, especially neutrophil collagenase, generated in such acne-affected skin, and by inhibiting other dermal matrix-degrading enzymes. This invention also inhibits the redness (erythema) and discomfort caused by the inflammatory reaction accompaning acne.

For the experiments, the results of which are shown in the figures described below, human volunteers (each having given informed consent) were used to assess the differences in collagenase and elastase concentration between areas of the skin having an acne lesion and uninvolved adjacent skin areas, and to evaluate ex vivo the likely effectiveness of certain inhibitors.

Figure 1:
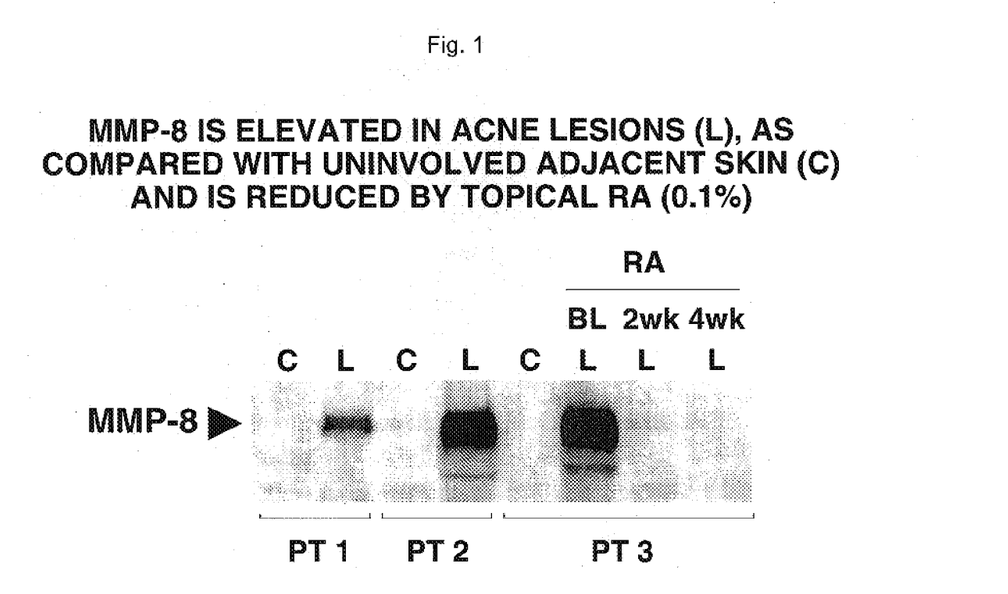
FIG. 1 depicts Western analysis of MMP-8 in human skin in vivo affected with an acne lesion, in uninvolved skin adjacent to the lesion.

FIG. 1 depicts a Western blot of MMP-8 collagenase protein in human skin biopsied from an area having an acne lesion (L in the figure) and from clear, uninvolved, adjacent areas of skin (C in the figure) in patients ("PT") 1, 2, and 3. As shown in this figure, all three patients clearly have MMP-8 present in the acne lesion, and have no MMP-8 present in unaffected, adjacent areas of skin.

Figure 2A:
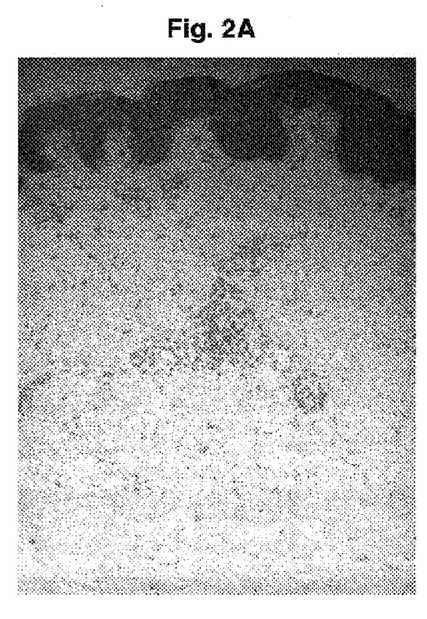
FIGS. 2A and 2B are photomicrographs of a skin biopsy of acne-affected skin and uninvolved skin from the same human volunteer, where the biopsies are stained to reveal the presence of neutrophil elastase.
Figure 2B:
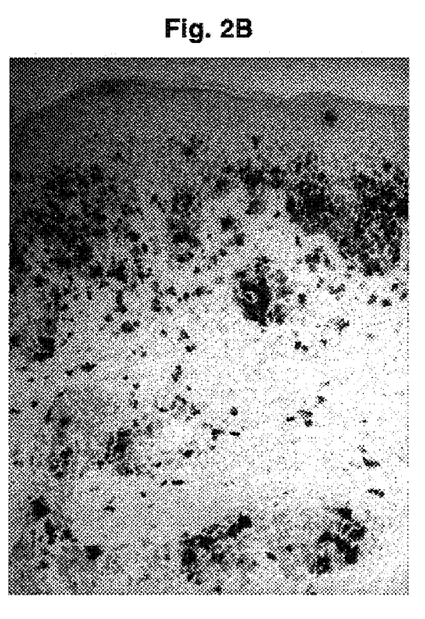

FIGS. 2A and 2B are photomicrographs of stained cross-section biopsies from human dermis and epidermis of a volunteer's skin. The photographic section on the right (2B) was taken through an acne lesion, and the one on the left (2A) was taken from normal, uninvolved skin. Each biopsy section was stained to show the presence of neutrophil elastase, a matrix-degrading serine protease. The presence of neutrophil elastase in FIG. 2B indicates the presence of neutrophils in the skin, presumably due (directly and/or indirectly) to the acne. The existence of neutrophil elastase in the skin would be expected to result in a breakdown of the elastin in the dermal matrix. Thus, we have found that acne-affected skin contains a significant amount of neutrophil elastase and that uninvolved skin contains essentially no neutrophil elastase. This finding indicates that the presence of acne causes the recruitment and infiltration of immune cells to acne-affected areas of the skin.

Figure 3A:
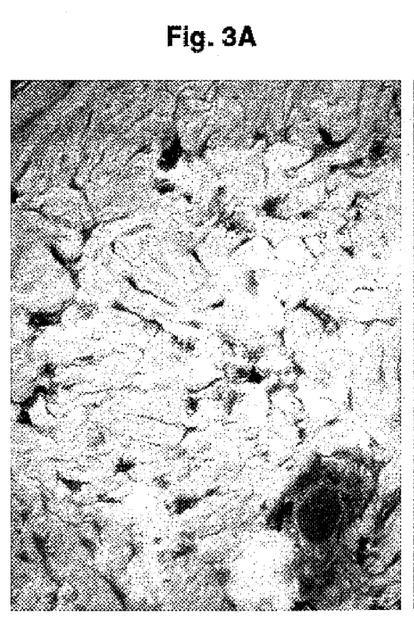
FIGS. 3A and 3B are photomicrographs of a skin biopsy of acne-affected skin and uninvolved skin from the same human volunteer, where the biopsies are stained to reveal the presence of MMP-1, FIGS. 3A and 3B being taken at a deeper level of the dermis.
Figure 3B:
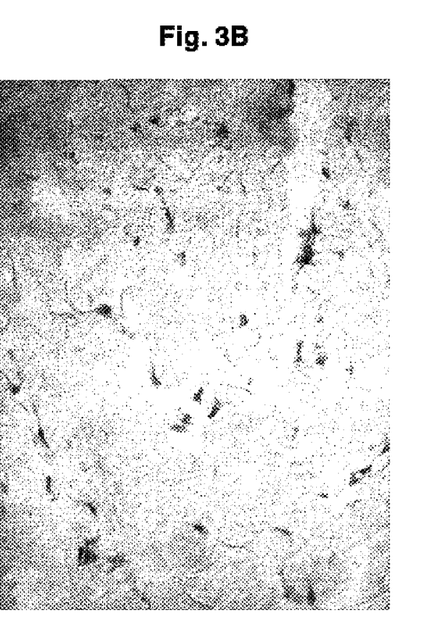

FIGS. 3A and 3B depict stained cross-sectional biopsies from a volunteer's acne-affected and uninvolved skin. The biopsies were taken and stained for the presence of collagenase (MMP-1). FIGS. 3A and 3B show biopsies from acne-affected (3A) and uninvolved (3B) skin that were taken from the lower dermis of a volunteer's skin. In these two figures, stained cells are seen (3A) from acne-affected skin at the level of the dermis, whereas no staining is found in the uninvolved skin (3B) at the same level of the dermis of uninvolved (not acne-affected) skin. Thus, we have found that acne induces collagenase in the dermis through skin cells (keratinocytes, fibroblasts) resident in the skin.

Figure 4A:
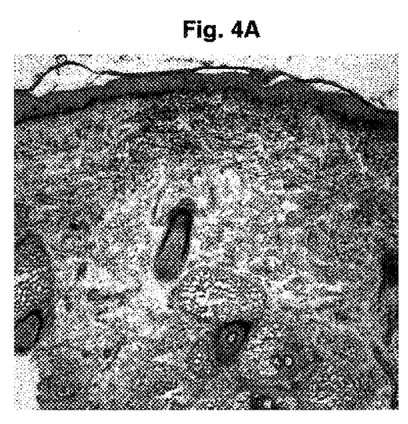
FIGS. 4A and 4B are color photomicrographs of a skin biopsy of uninvolved (4A) and acne-affected skin (4B), each having been stained to reveal the presence of Type I procollagen.
Figure 4B:
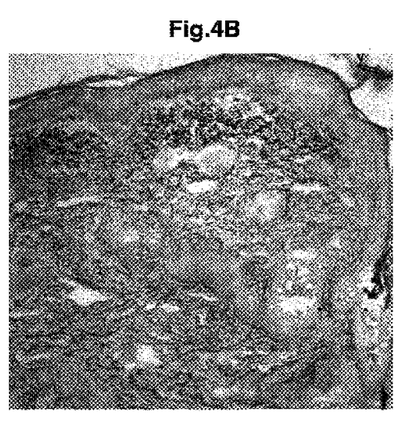

FIGS. 4A and 4B are photomicrographs of stained cross-sectional biopsies from the skin of a volunteer which have been stained for the presence of Type I procollagen; FIG. 4A is from non-acne-affected skin and FIG. 4B is from acne-affected skin. (The reader is referred to our co-pending application Ser. No. 285,860, filed 2 Apr. 1999, which describes preventing UV-induced inhibition of collagen biosynthesis in human skin, and our co-pending application Ser. No. 28,435, filed 24 Feb. 1998, regarding the reduced biosynthesis of procollagen in aged skin, and so are useful for a further understanding the significance of the lack of Type I procollagen; the disclosure of those applications is incorporated herein by reference for all purposes). The presence of Type I procollagen indicates that dermal cells are producing this collagen precursor, whereby the dermal matrix is being rebuilt by new collagen. (Procollagen is made in cells and is soluble; it passes into the dermal matrix where it is formed into insoluble collagen.) Uninvolved skin, as shown in FIG. 4A, is producing procollagen as would be expected, since acne generally starts affecting people in their teens, and these people typically have skin that is producing normal, significant amounts of procollagen. However, as shown in FIG. 4B, skin from the same subject as was taken for FIG. 4A, there is almost no procollagen production in acne-involved skin. Thus, we have found that acne-involved skin is deficient in procollagen production. As we discuss in our prior applications and patents regarding photoaging, exposure of human skin to UV radiation induces in that skin MMPs, and it is believed that imperfect repair of the skin after such MMP-inducing exposure leads to dermal scarring. Based on the present results, it would appear that scarring due to acne is significantly exacerbated by the absence of procollagen in the skin: although the skin is attempting to heal itself, the lack of procollagen in that skin means that there is likely to be an imperfect repair. Thus, the more acne-involved the skin, the less procollagen production, and, combined with the existence of increased amounts of MMPs in acne-involved skin, there is a greater probability of imperfect repair of the acne lesion.

Figure 5A:
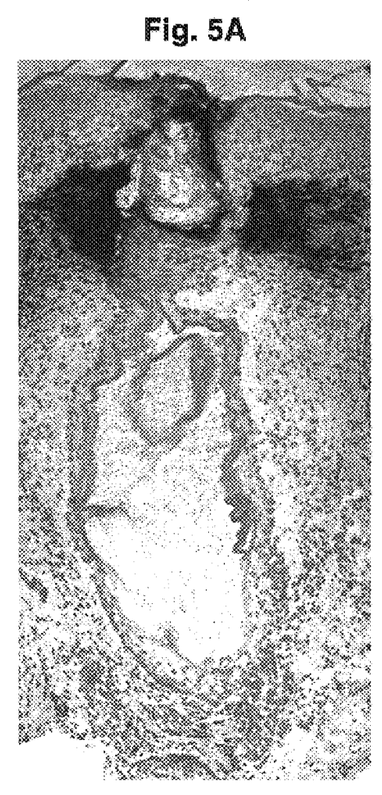
FIG. 5A is a photomicrograph of a skin biopsy of an acne lesion stained to reveal the presence of neutrophil elastase.
Figure 5B:
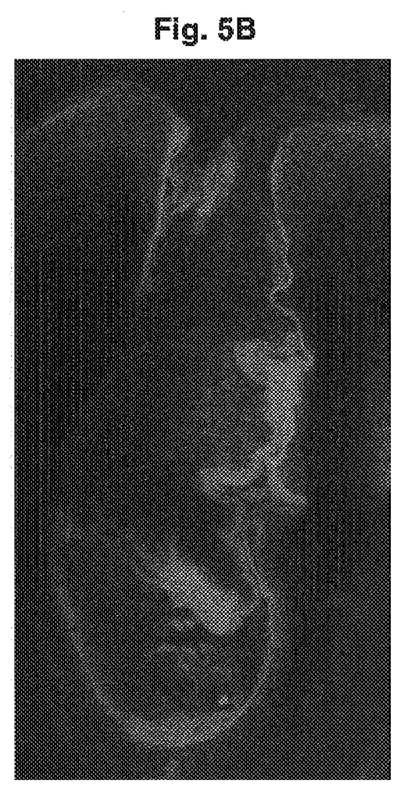
FIG. 5B is an in-situ zymogram showing neutrophil collagenase activity in an acne lesion.

FIG. 5A depicts acne-involved skin stained for neutrophil elastase. Neutrophils enter from the blood vessel (off the picture towards the bottom) and migrate to the surface of the skin (the epidermis being shown at the top of the panel). The staining is more significant at the top of the lesion in the dermis, while there is some staining (black dots) along the bottom portion of the lesion (suggesting that there are still other neutrophils migrating to the area). The other panel (FIG. 5B) is an in-situ zymogram showing the presence of collagenase activity; a section of the acne lesion is placed on a fluorescently-labelled collagen-coated slide, and where there is active collagenase that enzyme will destroy the fluorescently-labelled collagen on the slide and leave a black background on the panel. As seen in FIG. 5B, there was significant collagenase activity around the acne lesion. Thus, we have discovered that in the area of acne lesions there is neutrophil infiltration with significant elastase and collagenase activity.

While not desirous of being constrained to a particular theory, we believe that scarring due to acne is exacerbated, if not caused, by defects in skin repair. The skin is continuously trying to repair itself; in this instance from the degradation caused by acne. Acne, though more likely the bacterial infestation, leads to inflammation. The inflammatory response defense mechanism includes infiltration into the skin of neutrophil immune cells; these cells generate collagenase and elastase that degrade to dermal matrix, the degradation products being removed and the matrix then being repaired. This process of degradation, which is part of the repair process (i.e., the need to breakdown and remove materials for further repair and cell growth) is not perfect, and imperfections or defects in the repaired matrix can be manifest or presented as scars. Pursuant to the present invention, the administration of an inhibitor of a dermal matrix-degrading enzyme effective to affect acne-involved skin inactiviates these destructive proteins or eliminates their presence by blocking the pathway(s) that creates or activates them; whether topical or systemic, if the inhibitor is conveyed to the skin, it will be effective for inhibiting dermal matrix-degradaing enzymes and thus eliminates their consequences.

Figure 6:
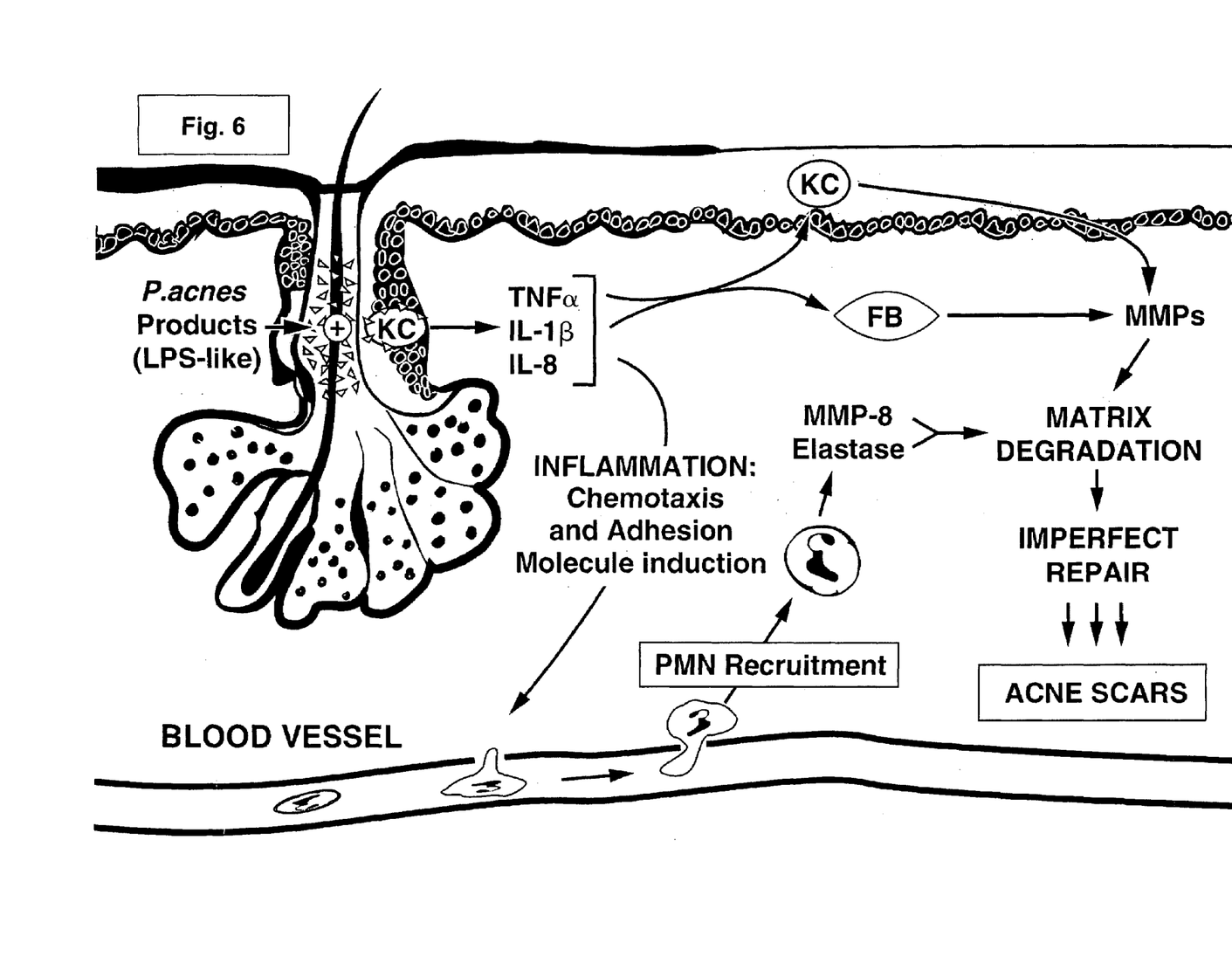
FIG. 6 is a cartoon depicting a possible mechanism for the present invention.

Again while not desirous of being constrained to a particular theory, the possible mechanism by which this invention functions is depicted in the cartoon of FIG. 6. On the left side of FIG. 6 a hair follicle infected with *P. acnes* is shown. These bacteria release LPS (lipopolysaccharide)-like compounds which are sensed by keratinocytes (KC) (triangles in FIG. 6). (B R Vowels, S Yang, and J J Leyden, "Induction of proinflammatory cytokines by a soluble factor of *Propionibacterium acnes*: implications for chronic inflammatory acne, *Infect. Immun.* 1995 63: 3158-3165; the disclosure of which is incorporated herein by reference). The toll-like receptor familty includes LPS receptors, and those in the keratinocytes are activated by LPS-like products from *P. acnes*. In turn, the keratinocytes release chemotactic factors, especially cytokines (IL-1β, IL-8, TNFα). These factors activate the AP-1 and NF-κB pathways, and NF-κB activates more IL-1 and TNFα (a cyclical process; see FIG. 1 in our prior patent U.S. Pat. No. 5,837,224 on photoaging due to UV radiation, the disclosure of which is incorporated herein by reference). The release of these factors causes inflammation, including the recruitment of neutrophils (PMNs; i.e., polymorphonuclear leukocytes) from the blood supply to the acne lesion; MMP-8 and elastase are preformed in the neutrophils and so their presence in skin is due to their presence in neutrophils. As shown in this cartoon, the cytokines also effect other keratinocytes and fibroblasts (FB), which are resident in the skin, to generate MMPs. The induction of matrix-degrading enzymes due to the presence of acne, and the continual repair of the damage they do, leads to imperfect repair of the skin. Thus, elimination of the enzymes that degrade the dermal matrix reduces imperfect repair of the skin, and so lessens scarring. As shown above in FIGS. 3A-3B, collagenase expression in acne-affected skin occurs in the dermis. Accordingly, a preferred composition includes indirect inhibitors of matrix degrading enzymes, such as glucocorticoids that block recruitment of neutrophils and other inflammatory immune cells, optionally retinoids that inhibit MMPs in resident skin cells, and direct inhibitors of these enzymes, such as serpine (a serine protease inhibitor analogous to TIMP), all preferably in combination with at least one compound for treating acne (e.g., benzoyl peroxide or tetracycline). While retinoids and antibacterials are commonly used to treat acne, they have not been used in combination with non-retinoid MMP inhibitors, elastase inhibitors, and/or inhibitors of the PNM recruitment pathway leading to degradation of the dermal matrix.

In light of our findings, acne-affected patients can be helped by decreasing the activity of matrix-degrading enzymes in the area of acne lesions. This can be accomplished by various means which are not mutually exclusive. One method is to disrupt the signalling caused by *P. acnes* byproducts that results in cytokines and MMPs. Another method is to disrupt the signalling that results in the recruitment of neutrophils with the accompanying neutrophil elastase and collagenase. Our present results suggest the mechanism shown in FIG. 6, a cartoon depicting the signalling in acne lesions. The *P. acnes* products induce keratinocytes (KC) to produce tumor necrosis factor alpha (TNFα), interlukin-1β (IL-1β), and interlukin-8 (IL-8), all cytokines. These cytokines induce resident skin cells to produce MMPs which degrade the dermal matrix. They also cause inflammation (e.g., redness, vasodilation, etc.) which is a signal for recruitment of neutrophils containing collagenase and elastase to the acne lesion; the neutrophil collagenase and the elastase contribute to degradation of the dermal matrix. The lack of procollagen biosynthesis, as shown in FIG. 4B, contributes to imperfect repair of the matrix. The end result is scarring.

To thwart the apparently inevitable result of acne scarring and inflammation, this invention disrupts the signalling pathways. More particularly, this invention uses an non-retinoid, non-steriod topically-applied composition, optionally in combination with a retinoid and/or a steriod, to inhibit this signalling, whereby degradation of the matrix is decreased and procollagen biosynthesis is restored, allowing the skin to heal with less scarring and less inflammation. Aspirin and E5510 (described by Fujimori, T., et at., Jpn J. Pharmacol (1991) 55(1):81-91) inhibit NF-κB activation. Farnesyl transferase inhibitors such as B-581 (described by Garcia A. M., et al., J Biol Chem (1993) 268(25):18415-18), BZA-5B (described by Dalton M. B. et al., Cancer Res (1995) 55(15):3295-3304), farnesyl acetate, and (α-hydroxyfarnesyl) phosphoric acid act on RAS and thus inhibit activation of the resultant ERK cascade; ERK leads to c-fos, which heterodimerizes with c-jun to create AP-1. Other useful inhibitors are those that inhibit NF-κB, such as sulfasalazine and parthenolide, serine protease (elastase) inhibitors, and antiadhesion molecules such as neutrophil infiltration inhibitors (e.g., selectin antagonists). As described in the aforementioned applications relating to UV-induction of MMPs, we have shown that so-called "antioxidants", like N-acetylcysteine (NAC), are useful at inhibiting MMPs, and have been shown in the literature (discussed below) to inhibit AP-1, NF-κB, and IL-8. Because the signalling that we have identified (which contributes to scarring and inflammation in acne) appears similar to the signalling by which UV irradiation induces MMPs, similar "antioxidants" as disclosed in those application and discussed below (e.g., NAC, FDO) are likely to be useful for combatting acne scarring and inflammation.

As used herein, "inhibitors" of MMPs and other dermal matrix-degrading enzymes, such as elastase, inhibit one or more of the steps in the natural physiological pathways leading to the production of these enzymes and/or directly inhibit one or more of these proteases, or they directly inhibit the activity of the enzyme. Thus, as used herein an "inhibitor" excludes retinoids, inasmuch as retinoids and tetracyclines have been known for treating acne, this invention is directed to the novel use of a non-retinoid enzyme inhibitor, which use may be combined with the conventional use of a retinoid and/or a tetracycline. Thus, an "inhibitor" is a non-retinoid compound that directly inhibits one or more dermal matrix-degrading enzymes and/or indirectly inhibits the enzyme by inhibiting some portion of an upstream pathway(s) leading to one or more of these dermal matrix-degrading enzymes. Inhibition of the upstream pathway of these dermal matrix-degrading enzymes includes inhibition of one or more of the various signalling compounds and/or of the transcription factors (e.g., NF-κB, or cJUN and cFOS which together create AP-1) by which these enzymes are produced naturally.

MMPs are also inhibited by BB2284 (described by Gearing, A. J. H. et al., Nature (1994) 370:555-557), GI129471 (described by McGeehan G. M., et al., Nature (1994) 370:558-561), and TIMPs (tissue inhibitors of metalloproteinases, which inhibit vertebrate collagenases and other metalloproteases, including gelatinase and stromelysin). Other compounds useful for the present invention are direct MMP inhibitors such as hydroxamate and hydroxy-urea derivatives, the latter exemplified by Galardin, Batimastat, and Marimastat, and those disclosed in EP-A1-0 558635 and EP-A1-0 558648 (disclosed as useful for inhibiting MMPs in the treatment of, among other etiologies, skin ulcers, skin cancer, and epidermolysis bullosa).

Indirect MMP inhibitors include kinase inhibitors genistein and quercetin (as described in U.S. Pat. Nos. 5,637,703, 5,665,367, and FR-A-2,671,724, the disclosures of which are incorporated herein by reference) and related compounds, as well as other antioxidants such as NAC (N-acetyl cysteine), discussed below. Still further, other kinase inhibitors are SB202190 (described by Lee, J. C., et al., Nature (1994) 372:739-746) and PD98059 (described by Dudley, D. T., et al., PNAS (USA) (1995) 92:7686-7689) inhibit specific kinases in the cascades, geranyl geranyltransferase inhibitors and lisofylline, which inhibit activation of the JNK cascade resulting from RAC/CDC42 activation, and U0126 (1,4-diamino-2,3-dicyano-1,4-bis[2-aminophenylthio]butadiene). As noted above, compounds that inhibit cytokines are indirect MMP inhibitors because interrupting the signalling pathway effectively inhibits MMPs. Compounds such as.

As mentioned, various compounds termed "antioxidants" are also useful as MMP inhibitors. While not desirous of being constrained to any particular theory of operation, these compounds may quench or otherwise reduce free radicals and reactive oxygen species which may initiate or lead to MMP induction, such as via the MAP kinase cascade. These compounds include glutathione and its precursors, such as N-acetyl cysteine (NAC) or glutathione ethyl ester, more broadly N—CH$_3$(CH$_2$)$_n$CO cysteine (wherein n is an integer from zero to eight, more preferably not more than 4), and related compounds and derivatives thereof as described in U.S. Pat. No. 5,296,500 (the disclosure of which is incorporated herein by reference). These other MMP inhibitors include water-soluble compounds such as vitamin C and NAC, and FDO. Various other compounds that may act as MMP inhibitors include: lipid-soluble compounds such as β-carotene and its derivatives or other carotenoids; glutathione and derivatives thereof (or of NAC); α-lipoic acid (1,2-dithiolane-3-pentanoic acid); selenium compounds such as Ebselen (2-phenyl-1,2-benzisoselenazol-3 (2H)-one); isoflavones such as genistein (isoflavone), quercetin (flavon-3-ol), and pycnogenol (flavan-3-ol(s)); ergothioneine; saponin (e.g., from *Polypodium leucotomos*); ginkgo biloba extract (flavoneglycoside and terpenelactone) and feverfew (*Chrysanthemum parthenium*) extract (sesquiterpene lactone).

Inhibitors of activator protein-1 (AP-1) are likely to inhibit the subsequent signalling that results in the presence of MMPs in the dermal matrix; the more of the pathway that is inhibited, the more likely there will be no induction of MMPs. Among various compounds that have been found to inhibit AP-1 and may likely be used topically include the following. Cannabinoids: Faubert and Kaminski; "AP-1 activity is negatively regulated by cannabinol through inhibition of its protein components, c-fos and c-jun", *J. Leukoc Biol*, vol. 67, no. 2 (2000 February, pp. 259-66) (Cannabinoid compounds exhibit immunosuppressive actions that are putatively mediated through Gi-protein coupled receptors that negatively regulate adenylate cyclase. However, recent studies suggest that cannabinoids modulate other signaling cascades. Cannabinol inhibited binding to AP-1-containing sites from the interleukin-2 promoter, in part, due to decreased nuclear expression of c-fos and c-jun. Thus, cannabinoid-induced immunosuppression involves disruption of the ERK signaling cascade.) Deferroxamine (DFO); Kramer-Stickland et al., "Inhibitory effects of deferoxamine on UVB-induced AP-1 transactivation", *Carcinogenesis*, vol. 20, no. 11, November 1999, pp. 2137-42 (Production of reactive oxygen species (ROS) by iron can contribute directly to DNA and protein damage and may contribute to cell signaling and proliferation. DFO treatment 24 h prior to UVB irradiation reduced UVB-induced AP-1 transactivation by approximately 80%, with the effect of DFO diminishing as pre-treatment time was shortened. Treatment with FeCl (3) a minimum of 6 h prior to UVB potentiated the UVB induction of AP-1 transactivation by 2-3-fold.) Separately, gadolinium chloride and alpha-tocopherol: Camandola et al., "Liver AP-1 activation due to carbon tetrachloride is potentiated by 1,2-dibromoethane but is inhibited by alpha-tocopherol or gadolinium chloride", *Free Radic Biol Med*, vol. 26, no. 9-10, May 1999, pp. 1108-16. Cyclosporin A: Sugano et al., "Cyclosporin A inhibits collagenase gene expression via AP-1 and JNK suppression in human gingival fibroblasts, *J. Periodontal Res*, vol. 33, no. 8, November 1998, pp. 448-452 (Cyclosporin A is able to affect signal transduction of lipidpolysaccharide-induced collagenase expression in fibroblasts; treatment of fibroblasts with LPS caused activation of collagenase gene, activator protein-1 (AP-1) and c-Jun N-terminal kinase (JNK). These activations were blocked by CsA. They suggest that inhibitory effects of CsA on LPS-induced signal transduction may contribute to the mechanism of CsA-induced gingival overgrowth. Catachins: Barthelman et al., "(–)-Epigallocatechin-3-gallate inhibition of ultraviolet B-induced AP-1 activity", *Carcinogenesis*, vol. 19, no. 12, December 1998, pp. 2201-4 (using cultured human keratinocytes, UVB-induced AP-1 activity is inhibited by EGCG in a dose range of 5.45 nM to 54.5 microM; EGCG is effective at inhibiting AP-1 activity when applied before, after or both before and after UVB irradiation; EGCG also inhibits AP-1 activity in the epidermis of a transgenic mouse model). Naphthopyranomycins and exfoliamycins, such as K1115 A (Naruse et al., "K1115A, a new anthraquinone that inhibits the binding of activator protein-1 (AP-1) to its recognition sites. II. Taxonomy, fermentation, isolation, physico-chemical properties and structure determination," *J. Antibiot* (Tokyo), vol 51, no. 6, June 1998, pp. 545-52; the anthraquinone 3,8-dihydroxy-1-propylanthraquinone-2-carboxylic acid). DHEA: Dashtaki et al., "Dehydroepiandrosterone and analogs inhibit DNA binding of AP-1 and airway smooth muscle proliferation", *J. Pharmacol Exp Ther*, vol. 285, no. 2, 1998 May (pp. 876-83) (dehydroepiandrosterone (DHEA) and its analogs such as 16-alpha-bromoepiandrosterone). Oleanolic acid glycosides: Lee et al., "Momordins inhibit both AP-1 function and cell proliferation," *Anticancer Res*, vol. 18, no. 1A, January-February 1999 (pp. 119-24). Monoterpene perillyl alcohol: Barthelman et al., "Inhibitory effects of perillyl alcohol on UVB-induced murine skin cancer and AP-1 transactivation", *Cancer Res*., vol. 58, no. 4, 15 Feb. 1998 (pp. 711-6). Curcumin, which inhibits both AP-1 and NF-κB: Xu et al., "Curcumin inhibits IL1 alpha and TNF-alpha induction of AP-1 and NF-κB DNA-binding activity in bone marrow stromal cells," *Hematopathol Mol Hematol*, vol. 11, no. 1, 1997-8 (pp. 49-62); and Pendurthi et al., "Suppression of activation of transcription factors Egr-1, AP-1, and NF-kappa B," *Arterioscler Thromb Vasc Biol*, vol. 17, no. 12, December 1997 (pp. 3406-13); and Bierhaus et al., "The dietary pigment curcumin reduces endothelial tissue factor gene expression by inhibiting binding of AP-1 to the DNA and activation of NF-kappa B," *Thromb Haemost*, vol. 77, no. 4, 1997 April (pp. 772-82). Aspirin (acetylsalicylic acid): Huang et al., "Inhibition of ultraviolet B-induced activator protein-1 (AP-1) activity by aspirin in AP-1-luciferase transgenic mice", *J. Biol Chem*, vol. 272, no. 42, 17 Oct. 1997 (pp. 26325-31). Pyrrolidine dithiocarbamate and N-acetyl cysteine (inhibit AP-1, NF-κB, and IL-8): Munoz et al., "Pyrrolidine dithiocarbamate inhibits the production of interleukin-6, interleukin-8, and granulocyte-macrophage colony-stimulating factor by human endothelial cells in response to inflammatory mediators: modulation of NF-kappa B and AP-1 transcription factors activity", *Blood*, vol. 88, no. 9, 1996 Nov. 1 (pp. 3482-90). Metal salts, such as gold (I) and selenite: Handel et al., "Inhibition of AP-1 binding and transcription by gold and selenium involving conserved cysteine residues in Jun and Fos," *Proc Natl Acad Sci USA*, vol. 92, no. 10, 1995 May 9 (pp. 4497-501) (in electrophoretic mobility-shift analyses, AP-1 DNA binding was inhibited by gold(I) thiolates and selenite, with 50% inhibition occurring at approximately 5 microM and 1 microM, respectively; and other metal ions inhibited at higher concentrations, in a rank order correlating with their thiol binding affinities); and Spyrou et al., "AP-1 DNA-binding activity is inhibited by selenite and selenodiglutathione", *FEBS Lett*, vol. 368, no. 1, Jul. 10, 1995 (pp. 59-63) (selenite and selenodiglutathione (GS-Se-SG)); and Williams et al., "Aurothioglucose inhibits induced NF-κB and AP-1 activity by acting as an IL-1 functional antagonist", *Biochim Biophys Acta*, vol. 1180, no. 1, Oct. 13, 1992 (pp. 9-14).

Elastase inhibitors include procyanidines and proanthocyanidines, which non-competitively inhibit the activities of the proteolytic enzymes collagenase ($IC_{50}$=38 nmol/l) and elastase ($IC_{50}$=4.24 nmol/l) (*Arzneimittelforschung* (GERMANY) May 1994, 44 (5) p 592-601), N-acetyl cysteine (e.g., U.S. Pat. No. 5,637,616 for a disclosure of NAC as an inhibitor of proteases that result in mucosal or skin lesions) and derivatives thereof (as described in our copending application 89,914, filed 3 Jun. 1998 (the disclosure of which is incorporated herein by reference)). Additional elastase inhibitors are described in the following disclosures. 6-Acylamino-2-(alkylsulfonyl)oxy-1H-isoindole-1,3-dione and related diones: Kerrigan et al., "6-Acylamino-2-(alkylsulfonyl)oxy-1H-isoindole-1,3-dione mechanism-based inhibitors of human leukocyte elastase", *Bioorg Med Chem Lett*, vol. 10, no. 1, Jan. 3, 2000 (pp. 27-30) (acylamino substitution in the 6-position increases selectivity and potency of these inhibitors for human leukocyte elastase); Gutschow et al., "2-(diethylamino)thieno-1,3-oxazin-4-ones as stable inhibitors of human leukocyte elastase", *J. Med Chem*, vol. 42, no. 26, Dec. 30, 1999 (pp. 5437-47) (2-(diethylamino)thieno[1,3]oxazin-4-one). Caffeic acid derivatives: Melzig et al., "Inhibition of granulocyte elastase activity by caffeic acid derivatives", *Pharmazie*, vol. 54, no. 9, 1999 September (pp. 712). Pyridyl esters of benzopyrans: Doucet et al., "6-Substituted 2-oxo-2H-1-benzopyran-3-carboxylic acid as a core structure for specific inhibitors of human leukocyte elastase", *J. Med Chem*, vol. 42, no. 20, Oct. 7, 1999 (pp. 4161-71). Certain beta-lactams: Taylor et al., "Novel mechanism of inhibition of elastase by beta-lactams is defined by two inhibitor crystal complexes", *J. Biol Chem*, vol. 274, no. 35, Aug. 27, 1999 (pp. 24901-5) (the presence of a hydroxyethyl substituent on the beta-lactam ring provides a new reaction pathway resulting in the elimination of the hydroxyethyl group and the formation of a stabilizing conjugated double bond system); Wilmouth et al., "Inhibition of elastase by N-sulfonylaryl beta-lactams: anatomy of a stable acyl-enzyme complex", *Biochemistry*, vol. 37, no. 50, Dec. 15, 1998 (pp. 17506-13); pyrrolidone trans-lactams and trans-lactones) such as disclosed by Macdonald et al., "Syntheses of trans-5-oxo-hexahydro-pyrrolo 3,2-bpyrroles and trans-5-oxo-hexahydro-furo 3,2-b-pyrroles (pyrrolidine trans-lactams and trans-lactones): new pharmacophores for elastase inhibition", *J. Med Chem*, vol. 41, no. 21, Oct. 8, 1998 (pp. 3919-22). Benzoyl aminoacetic acid derivatives: Sakuma et al., "ONO-5046 is a potent inhibitor of neutrophil elastase in human pleural effusion after lobectomy", *Eur J. Pharmacol*, vol. 353, no. 2-3, Jul. 24, 1998 (pp. 273-9) (sodium N-2-4-(2,2-Dimethylpropionyloxy)phenyl-sulfonylamino-benzoyl-aminoacetic acid). Complex sulfates: Fujie et al., "Release of neutrophil elastase and its role in tissue injury in acute inflammation: effect of the elastase inhibitor, FR134043", *Eur J. Pharmacol*, vol. 374, no. 1, Jun. 11, 1999 (pp. 117-25) (disodium-(Z,1S,15S,18S,24S,27R,29S,34S, 37R)-29-benzyl-21-ethylidene-27-hydroxy-15-isobutyrylamino-34-isopropyl-31, 37-dimethyl-10,16,19,22,30,32,35,38-octaoxo-36-oxa-9,11, 17,20,23,28,31,33-octaazatetracyclo 16,13,6,1(24,28)0(3, 8)-octatriconta-3,5,7-trien-5,6-diyl disulfate. Azaisochromens: Mitsuhashi et al., "Pharmacological activities of TEI-8362, a novel inhibitor of human neutrophil elastase", *Br J. Pharmacol*, vol. 126, no. 5, 1999 March (pp. 1147-52) (4-(N-(3-((3-carboxypropyl)amino)-8-methyl-1-oxo-4-azaisochromen-6-yl)carbamoyl)-4-((phenyl-methoxy)carbonylamino)butanoic acid ($C_{26}H_{28}N_4O_9$)). Acetamides: Yamano et al., "Protective effects of a PAF receptor antagonist and a neutrophil elastase inhibitor on multiple organ failure induced by cerulein plus lipopolysaccharide in rats", *Naunyn Schmiedebergs Arch Pharmacol*, vol. 358, no. 2, 1998 August (pp. 253-63) (2-(3-methylsulfonylamino-2-oxo-6-phenyl-1,2-dihydro-1-pyridyl)-N-(3,3,3-trifluoro-1-isopropyl-2-oxopropyl)acetamide). Molecules having only a few amino acid residues which are effective for penetrating the skin: Yamano et al., "Protective effect of a pancreatic elastase inhibitor against a variety of acute pancreatitis in rats" *Jpn J. Pharmacol*, vol. 77, no. 3, 1998 July (pp. 193-203) (trifluoroacetyl-L-lysyl-L-alaninanilide hydrochloride). Trifluoromethyl ketones: Huang et al., "Effect of trifluoromethyl ketone-based elastase inhibitors on neutrophil function in vitro", *J. Leukoc Biol*, vol. 64, no. 3, 1998 September (pp. 322-30) (new family of elastase inhibitors ICI200355 and ZD0892). Sulfone derivatives of thiazolidine-3-ones: Groutas et al., "Potent and specific inhibition of human leukocyte elastase, cathepsin G and proteinase 3 by sulfone derivatives employing the 1,2,5-thiadiazolidin-3-one 1,1 dioxide scaffold", *Bioorg Med Chem*, vol. 6, no. 6, 1998 June (pp. 661-71). Peptidyl trifluoromethylalcohols: Amour et al., "Stereoselective synthesis of peptidyl trifluoromethyl alcohols and ketones: inhibitory potency against human leukocyte elastase, cathepsin G, porcine pancreatic elastase and HIV-1 protease", *J. Pharm Pharmacol*, vol. 50, no. 6, 1998 June (pp. 593-600) (beta-peptidyl trifluoromethyl alcohols (TFMAs) Z-L-Val-NH-*CH(Y)*CH(OH)—$CF_3$, where *C is the chiral centre, varied in the nature of the substituent Y, a phenylethyl —$(CH_2)_2$—$C_6H_5$ or an isopropyl —$CH(CH_3)_2$ group; phenylethyl had $IC_{50}$=15 µM, whereas isopropyl had $IC_{50}$=200 µM). Benzoylamino acetates: Shinguh et al., "Biochemical and pharmacological characterization of FK706, a novel elastase inhibitor", *Eur J. Pharmacol*, vol. 337, no. 1, 1997 Oct. 15 (pp. 63-71) (FK706, sodium 2-4-(S)-1-(S)-2-(RS)-3,3,3-trifluoro-1-isopropyl-2-oxopropyl-aminocarbonyl-pyrrolidin-1-yl-carbonyl-2-methylpropyl-aminocarbonyl-benzoylamino acetate, $C_{26}H_{32}F_3N_4NaO_7$, a synthetic water-soluble inhibitor of human neutrophil elastase). Cephalosporin derivatives: Rees et al., "Inhibition of neutrophil elastase in CF sputum by L-658,758", *J. Pharmacol Exp Ther*, vol. 283, no. 3, 1997 December (pp. 1201-6); Buynak et al., "7-alkylidenecephalosporin esters as inhibitors of human leukocyte elastase", *J. Med Chem*, vol. 40, no. 21, Oct. 10, 1997 (pp. 3423-33) (7-alkylidene, 7-haloalkylidene, and 7-cyanomethylidene benzhydryl ester 7-(cyanomethylidene)cephalosporin sulfone derivatives). Azabicyclic compounds and perhydroindoles: Portevin et al., "Dual inhibition of human leukocyte elastase and lipid peroxidation: in vitro and in vivo activities of azabicyclo 2.2.2-octane and perhydroindole derivatives", *J. Med Chem*, vol. 40, no. 12, Jun. 6, 1997, (pp. 1906-18) (selective human leukocyte elastase (HLE) inhibitors of the Val-Pro-Val type in which the central proline residue was replaced by normatural amino acids Phi ((2S, 3aS, 7aS)-perhydroindole-2-carboxylic acid) and Abo((3S)-2-azabicyclo-2.2.2-octane-3-carboxylic acid). Trialkylammonium salts: Kouadri-Boudjelthia and Wallach, "Hydrophobic interactions are involved in the inhibition of human leukocyte elastase by alkyltrimethylammonium salts", *Int J. Biochem Cell Biol*, vol. 29, no. 2, 1997 February (pp. 353-9) (preferably alkyl chain longer than ten carbon atoms). Pivaloyloxy benzene derivatives: Imaki et al., "Non-peptidic inhibitors of human neutrophil elastase: the design and synthesis of sulfonanilide-containing inhibitors", *Bioorg Med Chem*, vol. 4, no. 12, 1996 December (pp. 2115-34) (sulfonanilide-containing analogues most promising). Functionalized N-aryl azetidin-2-ones: Joyeau et al., "Synthesis and inhibition of human leukocyte elastase by functionalized N-aryl azetidin-2-ones: effect of different substituents on the aromatic ring", *J. Pharm Pharmacol*, vol. 48, no. 12, 1996 December (pp. 1218-30) (N-aryl-3,3-difluoroazetidin-2-ones featured by a latent electrophilic methylene quinoniminium moiety, and incorporate on their aromatic ring either an alkyl moiety, a methoxy substituent or a carboxylic group; some proved to be good inactivators of human leukocyte elastase). Saccharine derivatives: Groutas et al., "Design, synthesis, and in vitro inhibitory activity toward human leukocyte elastase, cathepsin G, and proteinase 3 of saccharin-derived sulfones and congeners", *Bioorg Med Chem*, vol. 4, no. 9, 1996 September (pp. 1393-400) (derivatives has sulfinate leaving group; inhibitory activity is dependent on the nature and pKa of the leaving group, and the synthesized saccharin derivatives exhibit selective inhibition toward HLE). Mucopolysaccharides, such as heparin: Volpi, "Inhibition of human leukocyte elastase activity by heparins: influence of charge density", *Biochim Biophys Acta*, vol. 1290, no. 3, Aug. 13, 1996 (pp. 299-307) (heparins strongly inhibit elastase activity, and there is a significant linear dependence between charge density (sulfate-to-carboxyl ratio) and enzymatic activity). Exopolysaccharides: Ying et al., "Alginate, the slime exopolysaccharide of *Pseudomonas aeruginosa*, binds human leukocyte elastase, retards inhibition by alpha 1-proteinase inhibitor, and accelerates inhibition by secretory leukoprotease inhibitor", *Am J. Respir Cell Mol Biol*, vol. 15, no. 2, 1996 August (pp. 283-91) (data support a model in which each elastase molecule interacts with a total of 19 uronic acid units on the alginate, primarily through electrostatic forces).

NF-κB inhibitors include those disclosed in the following references. Cyclopentenone prostaglandins: Rossi et al., "Anti-inflammatory cyclopentenone prostaglandins are direct inhibitors of IkappaB kinase", *Nature*, vol. 403, no. 6765, Jan. 6, 2000 (pp. 103-8). Quercetin and staurosporine: Peet and Li, "Ikappab kinases alpha and beta show a random sequential kinetic mechanism and are inhibited by staurosporine and quercetin", *J. Biol Chem*, vol. 274, no. 46, Nov. 12, 1999 (pp. 32655-61) (but not the quercetin analogue Daidzein). Nepalolide A: Wang et al., "Nepalolide A inhibits the expression of inducible nitric oxide synthase by modulating the degradation of IkappaB-alpha and IkappaB-beta in C6 glioma cells and rat primary astrocytes", *Br J. Pharmacol*, vol. 128, no. 2, 1999 September (pp. 345-56). Turmeric (curcumin): Plummer et al., "Inhibition of cyclo-oxygenase 2 expression in colon cells by the chemopreventive agent curcumin involves inhibition of NF-kappaB activation via the NIK/IKK signalling complex", *Oncogene*, vol. 18, no. 44, Oct. 28, 1999 (pp. 6013-20). Salicylates: Stevenson et al., "Salicylic acid and aspirin inhibit the activity of RSK2 kinase and repress RSK2-dependent transcription of cyclic AMP response element binding protein- and NF-kappa B-responsive genes", *J. Immunol*, vol. 163, no. 10, Nov. 15, 1999 (pp. 5608-16). Diterpenes: de las Heras et al., "Inhibition of NOS-2 expression in macrophages through the inactivation of NF-kappaB by andalusol", *Br J. Pharmacol*, vol. 128, no. 3, 1999 October (pp. 605-12) (andalusol, ent-6α,8α,18-trihydroxy-13(16), 14-labdadiene, is a naturally occurring diterpene, isolated from *Sideritis foetens* (Lamiaceae). N-substituted benzamides: Liberg et al., "N-substituted benzamides inhibit NFkappaB activation and induce apoptosis by separate mechanisms", *Br J. Cancer*, vol. 81, no. 6, 1999 November (pp. 981-8). While not preferred due to potential toxicity issues, arsenic: Estrov et al., "Phenylarsine oxide blocks interleukin-1β-induced activation of the nuclear transcription factor NF-κB, inhibits proliferation, and induces apoptosis of acute myelogenous leukemia cells", *Blood*, vol. 94, no. 8, Oct. 15, 1999 (pp. 2844-53). Genistein: Tabary et al., "Genistein inhibits constitutive and inducible NFkappaB activation and decreases IL-8 production by human cystic fibrosis bronchial gland cells", *Am J. Pathol*, vol. 155, no. 2, 1999 August (pp. 473-81). Theophylline: Tomita et al., "Functional assay of NF-kappaB translocation into nuclei by laser scanning cytometry: inhibitory effect by dexamethasone or theophylline", *Naunyn Schmiedebergs Arch Pharmacol*, vol. 359, no. 4, 1999 April (pp. 249-55). Cepharanthine: a plant alkaloid (I) (Merck Index 11, 306, 1981), and described in U.S. Pat. Nos. 2,206,407 and 2,248,241, and Japanese Patents 120, 483, 128,533, and 141,292. Trifluoroalkyl salicylates: Bayon et al., "4-trifluoromethyl derivatives of salicylate, triflusal and its main metabolite 2-hydroxy-4-trifluoromethylbenzoic acid, are potent inhibitors of nuclear factor kappaB activation", *Br J. Pharmacol*, vol. 126, no. 6, 1999 March (pp. 1359-66) (2-hydroxy-4-trifluoromethylbenzoic acid (HTB) and 2-acetoxy-4-trifluoromethylbenzoic acid (triflusal), both more potent than aspirin or salicylate as inhibitors of NF-κB, indicating that the incorporation of a 4-trifluoromethyl group to the salicylate molecule strongly enhances its inhibitory effect on NF-κB activation). Quinapril: quinapril hydrochloride is chemically described as [3S-[2[R*(R*)], 3R*]]-2-[2-[[1-(ethoxycarbonyl)-3-phenylpropyl]amino]-1-oxopropyl]-1,2,3,4-tetrahydro-3-isoquinolinecarboxylic acid, monohydrochloride. Its empirical formula is $C_{25}H_{30}N_2O_5 \cdot HCl$. Cyclosporine A: Meyer et al., "Cyclosporine A is an uncompetitive inhibitor of proteasome activity and prevents NF-kappaB activation", *FEBS Lett*, vol. 413, no. 2, 1997 Aug. 18 (pp. 354-8). Arachidonic acid derivatives: Thommensen et al., "Selective inhibitors of cytosolic or secretory phospholipase A2 block TNF-induced activation of transcription factor nuclear factor-kappa B and expression of ICAM-1", *J. Immunol*, vol. 161, no. 7, 1998 Oct. 1 (pp. 3421-30) (TNF-induced activation of NF-κB inhibited by trifluoromethyl ketone analogue of arachidonic acid ($AACOCF_3$), methyl arachidonyl fluorophosphate, trifluoromethyl ketone analogue of eicosapentaenoic acid ($EPACOCF_3$), 12-epi-scalaradial, and LY311727; arachidonyl methyl ketone analogue ($AACOCH_3$) and the eicosapentanoyl analogue ($EPACHOHCF_3$) had no effect on TNF-induced NF-κB activation. Genistein, erbstatin: Natarajan et al., "Protein tyrosine kinase inhibitors block tumor necrosis factor-induced activation of nuclear factor-κB, degradation of IκBα, nuclear translocation of p65, and subsequent gene expression", *Arch Biochem Biophys*, vol. 352, no. 1, Apr. 1, 1998 (pp. 59-70). Fasudil: 1-(5-isoquinolinesulfonyl)homopiperazine hydrochloride (fasudil hydrochloride); Sato et al., "Inhibition of human immunodeficiency virus type 1 replication by a bioavailable serine/threonine kinase inhibitor, fasudil hydrochloride", *AIDS Res Hum Retroviruses*, vol. 14, no. 4, Mar. 1, 1998 (pp. 293-8). ACE (angiotensin converting enzyme) inhibitors, like quinipril: Hernandez-Presa et al., "Angiotensin-converting enzyme inhibition prevents arterial nuclear factor-kappa B activation, monocyte chemoattractant protein-1 expression, and macrophage infiltration in a rabbit model of early accelerated atherosclerosis", *Circulation*, vol. 95, no. 6, Mar. 18, 1997 (pp. 1532-41). Synthetic 1,3,7-trialkyl xanthine derivatives, such as pentoxifylline (3,7-dimethyl-1-(5-oxohexyl)xanthine; Drugs & Aging 1995, 7/6: 480-503) and denbufylline (1,3-dibutyl-7-(2-oxopropyl)xanthine); Lee et al., "Pentoxifylline blocks hepatic stellate cell activation independently of phosphodiesterase inhibitory activity", *Am J. Physiol*, vol. 273, no. 5 Pt 1, 1997 November (pp. G1094-100). Benzophenanthradine derivatives: Chaturvedi et al., "Sanguinarine (pseudochelerythrine) is a potent inhibitor of NF-κB activation, IκBα phosphorylation, and degradation", *J. Biol Chem*, vol. 272, no. 48, Nov. 28, 1997 (pp. 30129-34) (sanguinarine, a benzophenanthridine alkaloid). Actinomycin D: Faggioli et al., "Protein synthesis inhibitors cycloheximide and anisomycin induce interleukin-6 gene expression and activate transcription factor NF-κB", *Biochem Biophys Res Commun*, vol. 233, no. 2, Apr. 17, 1997 (pp. 507-13) (IL-6 mRNA accumulation in two human cell lines, MDA-MB-231 and HeLa, stimulated by cycloheximide or anisomycin is almost completely inhibited in the presence of actinomycin D). Hydroxyanthranilic acids: Sekkai et al., "Inhibition of nitric oxide synthase expression and activity in macrophages by 3-hydroxyanthranilic acid, a tryptophan metabolite", *Arch Biochem Biophys*, vol. 340, no. 1, Apr. 1, 1997 (pp. 117-23) (3-hydroxyanthranilic acid but not anthranilic acid). Nordihydroguaiaretic acid and AA861: Lee et al., "Inhibition of 5-lipoxygenase blocks IL-1 beta-induced vascular adhesion molecule-1 gene expression in human endothelial cells", *J. Immunol*, vol. 158, no. 7, Apr. 1, 1997 (pp. 3401-7). Prostaglandin A1: Rossi et al., "Inhibition of nuclear factor kappa B by prostaglandin A1: an effect associated with heat shock transcription factor activation", *Proc Natl Acad Sci USA*, vol. 94, no. 2, Jan. 21, 1997 (pp. 746-50).

Sialyl Lewis X (SLe.sup.x) mediates binding of neutrophils to vascular endothelial cells by binding to E-selectin. (M. Phillips, et al., *Science* 1990, 250, 1130; J. Lowe, et al., Cell 1990, 63, 475; T. Feizi, *Trends Biochem Sci* 1991, 16, 84; M. Tiemeyer., et al., *Proc. Natl. Acad. Sci. USA* 1991, 88, 1138; L. Lasky, *Science* 1992, 258, 964; and T. Springer, L. A. Lasky, *Nature* 1991, 349, 196.) Sialyl Lewis X (SLe.sup.x) is a cell surface carbohydrate ligand found on neutrophils, anchored onto the outer membrane thereof by integral membrane glycoproteins and/or glycolipids. Administration of SLe.sup.x inhibits the SLe.sup.x/E-selectin interaction and blocks adhesion of neutophils to endothelial cells. (M. Buerke, et al., *J. Clin. Invest.*, 1994, 1140). Neutrophil-mediated inflammatory diseases may be treated by administration of Sialyl Lewis X (SLe.sup.x). Selectin inhibitor include those in the following references. E-, P-, and L-selectin inhibitors in U.S. Pat. No. 5,830,871. Sulfatides and sialylated or sulfated fucooligosaccharides, as described in U.S. Pat. No. 5,985,852, and other fucose derivatives as described in U.S. Pat. Nos. 5,962,422 and 5,919,769; as well as described by Ikami et al., "Synthetic studies on selectin ligands-inhibitors: Synthesis and inhibitory activity of 2-O-fucosyl sulfatides containing 2-branched fatty alkyl residues in place of ceramide", *Journal of Carbohydrate Chemistry*, vol. 17, no. 3, 1998 (pp. 453470) (sulfated 2-O-alpha-L-fucopyranosyl beta-D-galactopyranosides containing 2-branched fatty-alkyl residues in place of ceramide); Todderud et al., "BMS-190394, a selectin inhibitor, prevents rat cutaneous inflammatory reactions", *J. Pharmacol Exp Ther*, vol. 282, no. 3, 1997 September (pp. 1298-304) (selectin antagonist BMS-190394, a structural analog of sulfatide). TBC-1269 (available from Texas Biotechnology Corp., Houston, Tex.) and other mannose derivatives: for example, Dupre et al., "Glycomimetic selectin inhibitors: (alpha-D-mannopyranosyloxy)methylbiphenyls", *Bioorganic & Medicinal Chemistry Letters*, vol. 6, no. 5, 1996 (pp. 569-572); Lin et al., "Synthesis of sialyl Lewis x mimetics as selectin inhibitors by enzymatic aldol condensation reactions", *Bioorg Med Chem*, vol. 7, no. 3, 1999 March (pp. 425-33) (D-mannosyl phosphate/phosphonate derivatives enzymatically prepared as sialyl Lewis x tetrasaccharide mimics); Kogan et al., "Rational design and synthesis of small molecule, non-oligosaccharide selectin inhibitors:(alpha-D-mannopyranosyloxy)-biphenyl-substituted carboxylic acids", *J. Med Chem*, vol. 38, no. 26, Dec. 22, 1995 (pp. 4976-84). Leumedins: Endemann et al., "Novel anti-inflammatory compounds induce shedding of L-selectin and block primary capture of neutrophils under flow conditions", *J. Immunol* May 15, 1997; 158(10):4879-85 (leumedins are small molecules that inhibit neutrophil movement into inflamed tissues). Di- and tri-valent small molecules, mainly 3-carboxyaralkyl-substituted 2-α-D-mannopyranosyloxy-phenyl unsubstitued, oxygen-, or nitrogen-substituted alkanes (e.g., oxobutane, piperidine), as described in U.S. Pat. No. 5,919, 768. GSC-150: Wada et al., "Effect of GSC-150, a new synthetic selectin inhibitor, on skin inflammation in mice", *Japanese Journal of Pharmacology*, vol. 71, no. Suppl. 1, 1996 (Page 302P). Sialyl Lewis x analogs: Kiso et al., "Studies of selectin binding inhibitors: Synthesis of sialyl-Lewis x and sialyl-Lewis a epitope analogs containing 2-acetamido derivative of N-methyl-1-deoxynojirimycin", *Journal of Carbohydrate Chemistry*, vol. 15, no. 1, 1996 (pp. 1-14) (synthesis of sialyl-Lewis x (15) and sialyl-Lewis a (17) epitope analogs containing the 2-acetamido derivative of N-methyl-1-deoxynojirimycin). Glycolipid sulfatide: Nair et al., "Inhibition of immune complex-induced inflammation by a small molecular weight selectin antagonist", *Mediators of Inflammation*, vol. 3, no. 6, 1994 (pp. 459-463). Triterpene glucosides such as glycyrrhizin: Rao et al., "Glycyrrhetinic acid glycosides are sialyl Lewis X mimics, and function as selectin inhibitors", *Molecular Biology of the Cell*, vol. 5, no. Suppl., 1994 (pp. 480A); Narasinga et al., "Sialyl Lewis X Mimics Derived from a Pharmacophore Search Are Selectin Inhibitors with Anti-inflammatory Activity", *Journal of Biological Chemistry*, vol. 269, no. 31, 1994 (pp. 19663-19666) (glycyrrhizin, an L-fucose derivative, and a C-fucoside derivative; Subramanian et al., "Attenuation of renal ischemia-reperfusion injury with selectin inhibition in a rabbit model", *Am J. Surg*, vol. 178, no. 6, 1999 December (pp. 573-6). GM-1925: Cornell and Bowyer, "Attenuation of lung injury in a rabbit acid aspiration model using GM-1925, a novel selectin inhibitor", *Surgical Forum*, vol. 45, 1994 (pp. 107-110). Diisopropyl fluorophosphate: Palecanda et al., "Complete inhibition of cross-linking and activation induced shedding of 1 selectin by the serine protease inhibitor diisopropyl fluorophosphate DPF", *J. Immunol*, vol. 150, no. 8 Part 2, 1993 (page 304A). BR 44-09 and BR 44-096837: Heavner et al., "Multiple binding site involvement in neutrophil selectin adhesion implications for design of peptide and carbohydrate inhibitors BIO BR 44-09 BR 44-096840", *J. Cell Biochem Suppl*, no. 17 Part A, 1993 (p. 342); Dalton et al., Inhibition of selectin mediated adhesion in-vivo and in-vitro BIO BR 44-09 BR 44-096837", *J. Cell Biochem Suppl*, no. 17 Part A, 1993 (p. 342). GMP-140: May et al., "GMP-140 P Selectin inhibits human neutrophil activation by lipopolysaccharide analysis by proton magnetic resonance spectroscopy BIO BA 93-00 BA 93-130631", *Biochem Biophys Res Commun*, vol. 183, no. 3, 1992 (pp. 1062-1069). Tetrasaccharides: Ushakova et al., "Inhibitory activity of monomeric and polymeric selectin ligands", *Vopr Med Khim*, vol. 45, no. 5, 1999 September-October (pp. 375-83) (tetrasaccharides SiaLex, SiaLea, HSO$_3$Lex, their conjugates with polyacrylamide (40 kDa), and several other monomeric and polymeric substances; all monomeric inhibitors were about two orders of magnitude weaker; PAA-conjugates, containing as a ligand tyrosine-o-sulfate in addition to one of the above mentioned oligosaccharides, were the most potent synthetic blockers compared with fucoidan, bi-ligand glycoconjugate HSO3Lea-PAA-sTyr); Bertozzi et al., "Sulfated disaccharide inhibitors of L-selectin: deriving structural leads from a physiological selectin ligand", *Biochemistry*, vol. 34, no. 44, 1995 Nov. 7 (pp. 14271-8) (generated a simple small molecule (lactose 6',6-disulfate) with greater inhibitory potency for L-selectin than sialyl Lewis x). Panosialins: Shinoda et al., "Panosialins, inhibitors of an alpha1,3-fucosyltransferase Fuc-TVII, suppress the expression of selectin ligands on U937 cells", *Glycoconj J.*, vol. 15, no. 11, 1998 November (pp. 1079-83). CY-1503: Schmid et al., "Carbohydrate selectin inhibitor CY-1503 reduces neutrophil migration and reperfusion injury in canine pulmonary allografts", *J. Heart Lung Transplant*, vol. 16, no. 10, 1997 October (pp. 1054-61).

Generally, molecules having a molecular weight of less than about 600 will pass through the skin, and lipophilic molecules are preferred (or a conjugate having a lipophilic portion). Accordingly, while short chain peptides are not listed above, those having a low molecular weight and a high proportion of lipophilic amino acid residues are likely to be useful as topical inhibitors of AP-1, NF-κB, elastase, and/or selectin.

Figure 7A:
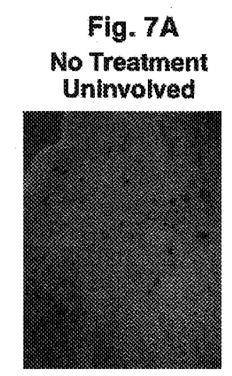
FIGS. 7A-7F are photomicrographs of zymograms of skin biopsies showing the presence (or absence) of collagenase activity in uninvolved skin (7A), untreated acne-affected skin (7B), control-treated acne-affected skin (7C), and in treated acne-affected skin (7D-7F).
Figure 7B:
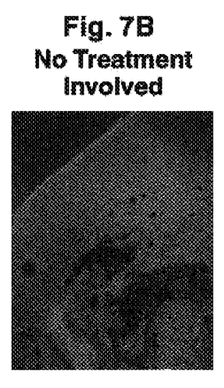
Figure 7C:
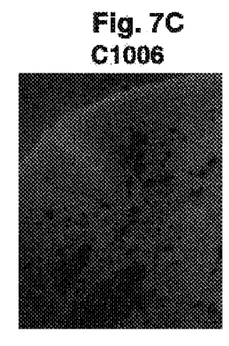
Figure 7D:
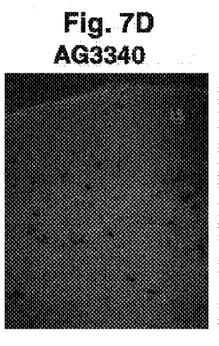
Figure 7E:
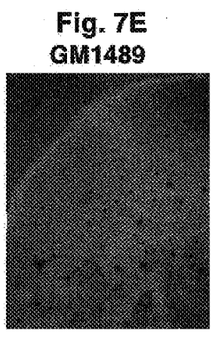
Figure 7F:
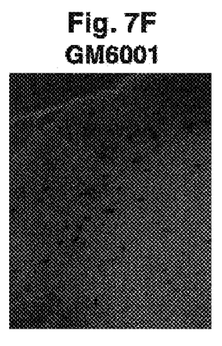

FIGS. 7A-7F show the effect of a control and some of these inhibitors on acne-affected skin. Each of these figures is an in-situ zymogram showing collagenase (MMP-1 and/or MMP-8) activity in a biopsied section; green is fluorescently-labelled collagen placed on a slide, over which is placed a biopsy section from an acne lesion from a human volunteer. FIG. 7A is a zymogram of a biopsy of uninvolved (not acne-affected) skin; there is almost no collagenase activity. FIG. 7B is a zymogram of acne-involved skin; there is significant collagenase activity as evidenced by the dark (black) areas where the fluorescently-labelled collagen has been degraded by the collagenase in the biopsied specimen. FIG. 7C is a zymogram of acne-involved skin which was treated with a control compound C1006 structurally analogous to known inhibitors but found to be inactive (the subject compound is applied over the biopsy section laid on the fluorescently-labelled collagen-coated slide); as seen by the dark areas, there was still significant collagen degradation (and hence collagenase activity). FIG. 7D is a zymogram of acne-affected skin treated with a collagenase inhibitor AG 3340 (Drugs R D 1999 February; 1(2):137-8); the amount of collagenase activity is minimal and comparable with that seen for uninvolved skin. FIG. 7E is also a zymogram of acne-involved skin treated with collagenase inhibitor GM 1489; again there is significant inhibition of collagenase activity. Finally, FIG. 7F is a zymogram of acne-involved skin treated with GM6001; again there is significant suppression of collagenase activity. The MMP inhibitor GM6001 is N-[(2R)-2-hydroxamidocarbonylmethyl)-4-methylpentanoyl]-L-tryptophan methylamide (ilomastat) (see RE Galardy et al., *Ann. NY Acad. Sci.*, 732: 315-323 (1994)). The inhibitor GM1489 is N-[(2R)-2-(carboxymethyl)-4-methylpentanoyl]-L-tryptophan methylbenzylamide (see W M Holleran et al., (1997) *Arch. Dermatol. Res.* 289:138-144). The control compound C1006 is N-t-Butyloxycarbonyl-L-leucyl-L-tryptophan methylamide. These three compounds (GM6001, GM1489, and C1006, were obtained from AMS Scientific Inc., Concord, Calif.).

The compositions of this invention can be provided in any cosmetically suitable form, preferably as a lotion or cream, but also in an ointment or oil base, as well as a sprayable liquid form (e.g., a spray that includes the MMP inhibitor in a base, vehicle, or carrier that dries in a cosmetically acceptable way without the greasy appearance that a lotion or ointment would have if applied to the skin).

In addition, the compositions contemplated by this invention can include one or more compatible cosmetically acceptable adjuvants commonly used, such as colorants, fragrances, emollients, humectants, and the like, as well as botanicals such as aloe, chamolile, and the like.

When used topically, an inhibitor (of a dermal matrix-degrading enzyme) is used preferably at concentrations of between about 0.05% and about 5%, more preferably between 0.1% and 1%; antioxidants are preferably taken in "megadoses" (e.g., at least 1 g/d of vitamin C, at least 1000 I.U. of one or more tocopherols). A direct inhibitor includes AG3340, used at 0.3%±0.1%.

In view of the foregoing, another facet of this invention is the use of an MMP inhibitor in combination with a clinical therapy for acne. The various treatments for acne, as noted in the Background section, involve the topical or oral administration of any number of active ingredients, ranging from antibacterials to anti-inflammatories. By virtue of this invention, combination therapies, such as combined oral and topical administration of tetracycline (which may involve use of two different tetracyclines), combined oral and topical administration of a retinoid, or a combination topical composition containing (i) an MMP inhibitor and/or an elastase inhibitor and (ii) another compound (such as an antibiotic, comedolytic, and/or anti-inflammatory).

In another aspect this invention includes an improved process for treating acne. As mentioned above, retinoids are known and presently used for treating acne. According to this invention, the improvement to that process is the use of a compound that inhibits the degradation of the retinoid. One enzyme that degrades retinoids and can be inhibited is cytochrome P-450. In the skin, retinoids are converted into retinoic acid (RA) as the active form. Natural retinoids that function in the skin are all trans or are metabolized to all trans. Retinoic acid (RA; all trans) is metabolized to inactivation by hydroxylation (via RA 4-hydroxylase) to 4-hydroxy-RA, which is then oxidized by a reaction mediated by the cytochrome P-450-dependent monooxygenase system. (S. Kang et al., "Liarozole Inhibits Human Epidermal Retinoic Acid 4-Hydroxylase Activity and Differentially Augments Human Skin Responses to Retinoic Acid and Retinol In Vivo," *J. Invest. Dermatol.*, 107:183-187 (August 1996); E. A. Duell et al., "Human Skin Levels of Retinoic Acid and Cytochrome P-450-derived 4-Hydroxyretinoic Acid after Topical Application of Retinoic Acid In Vivo Compared to Concentrations Required to Stimulate Retinoic Acid Receptor-mediated Transcription In Vitro," *J. Clin. Invest., Skin Retinoid Levels and Reporter Gene Activity,* 90:1269-1274 (October 1992); E. A. Deull et al., "Retinoic Acid Isomers Applied to Human Skin in Vivo Each Induce a 4-Hydroxylase That Inactivates Only Trans Retinoic Acid," *J. Invest. Dermatol.*, 106:316-320 (February 1996); the disclosures of which are incorporated herein by reference). Accordingly, compounds which interfere with the elimination metabolism of all trans RA, the active metabolite of topically applied retinoids such as 9-cis RA and 13-cis RA, will beneficially increase the amount of RA in the skin. Thus, preventing the degradation of natural (all trans) RA in the skin effectively increases its concentration, and so provides the benefits useful for its treatment of acne.

Retinoids that are or may likely be useful for treating acne include natural and synthetic analogs of vitamin A (retinol), vitamin A aldehyde (retinal), vitamin A acid (retinoic acid (RA)), including all-trans, 9-cis, and 13-cis retinoic acid), etretinate, and others as described in EP-A2-0 379367, U.S. Pat. Nos. 4,887,805, and 4,888,342 (the disclosures of which are all incorporated herein by reference), and the dissociating retinoids that are specific for AP-1 antagonism (such as those described by Fanjul, et al. in Nature (1994) 372:104-110). Various synthetic retinoids and compounds having retinoid activity are expected to be useful in this invention, to the extent that they exhibit anti-MMP activity in vivo, and such are described in various patents assigned on their face to Allergan Inc., such as in the following U.S. Pat. Nos. 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos., numbered: 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like, the disclosures of all of the foregoing and following patents and literature references hereby incorporated herein by reference.

Examples of compounds dermatologically acceptable and having or likely to have inhibitory effects on the P-450-mediated degradation of RA and other retinoids include azoles, especially triazoles, including, for example, ketoconazole (U.S. Pat. Nos. 4,144,346 and 4,223,036), fluconazole (U.S. Pat. No. 4,404,216), itraconazole (U.S. Pat. No. 4,267,179), liarozole, irtemazole, and the like; compounds related to these that may also be useful include, for example, diazines such as flucytosine.

It would also be beneficial to use such cytochrome P-450 inhibitors in combination with a reduced amount of retinoid; the P-450 inhibitor decreases the metabolic elimination of the retinoid and so less retinoid is needed to achieve the same result. Still further, analytical methods are available for determining whether a given compound inhibits the degradation of RA by applying the compound and testing for changes in CRABP (cytoplasmic retinoic acid binding protein), which will have increased levels if the levels of RA are also increased by the topical application of the test compound.

METHODS USED IN THE EXAMPLES

The references noted in this section are incorporated herein by reference.

Preparation of skin supernatants for biochemical analysis. Skin samples were ground by mortar and pestle under liquid nitrogen, and homogenized in a Dounce tissue grinder in buffer containing 10 mM Hepes, 1 nM EDTA, 5 mM EGTA, 10 mM $MgCl_2$, 50 mM glycerophosphate, 5 mM $NaVO_4$, 2 mM DTT, 0.5 mM PMSF, 10 µg/ml aprotinin, 10 µg/ml leupeptin, and 10 µg/ml pepstatin, and 0.5% NP-40. Homogenates were centrifuged at 14,000 g for 15 min., and supernatants were collected and used for biochemical determinations as described herein.

Immunohistology: Immunihistology of Type I pN collagen, MMP-1, and neutrophil elastasewere performed as has been described by Griffiths, C. E. M., et al., *N. Engl. J. Med.*, 329:530-535 (1993). Type I pN collagen was detected with mouse monoclonal IgG1 antibody (SP1.D8; available from Univ. of Iowa Dept. of Biological Sciences Developmental Studies Hybridoma Bank, Iowa City, Iowa) raised against the aminopropeptide region of human Type I procollagen (Foellmer, H. G., et al., *Euro. J. Biochm.*, 134:183-189 (1983)). The MMP-1 antibody is available from Comicon (Temecula, Calif.), and the neutrophil elastase antibody is available from DAKO (Carpinterina, Calif.).

Western analysis of proteins. Immunoreactive proteins were visualized by enhanced chemiluminescence detection and quantified by laser densitometry, or by enhanced chemifluorescence detection and quantified by a Storm imager (Molecular Dynamics, Palo Alto, Calif.).

In-situ Zymography: performed as described by Fisher et al. in "Pathophysiology of premature skin aging induced by ultraviolet radiation," *New Engl. J. Med.*, vol. 337, pp. 1419-1428 (1997).

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A method for treating acne-affected skin, comprising the steps of: orally administering an active ingredient for the treatment of acne selected from the group consisting of retinoids, tetracyclines, derivatives thereof, and mixtures thereof; and topically administering to the acne-affected skin a composition comprising a non-retinoid, non-glucocorticoid inhibitor of at least one of MMP-1 and MMP-8 and is selected from the group consisting of NF-κB inhibitors, adhesion antagonists, and compatible mixtures thereof.

2. The method of claim 1, wherein the inhibitor of MMP-1 or MMP-8 is applied regularly from once every two days to twice daily.

3. The method of claim 2, wherein the topical composition is applied daily.

4. The method of claim 1, wherein the composition further comprises an elastase inhibitor.

5. The method of claim 1, wherein the topical composition further comprises an AP-1 inhibitor of MMP-1.

6. The method of claim 1, wherein the active ingredient is a retinoid.

7. The method of claim 6, wherein the active ingredient is retinoic acid.

8. The method of claim 7, wherein the active ingredient is 13-cis-retinoic acid.

9. The method of claim 1, wherein the topical composition comprises E5510.

10. The method of claim 1, wherein the topical composition further comprises an isoflavone.

11. The method of claim 1, wherein the inhibitor is an NF-κB inhibitor selected from the group consisting of cyclopentenone prostaglandins, queretin, genistein, sulfasalazine, aspirin, staurosporine, curcumin, erbstatin, quinapril, 2-hydroxy-4-trifluoromethylbenzoic acid, 2-acetoxy-4-trifluoromethylbenzoic acid, and an arachidonic acid derivative.

12. The method of claim 1, wherein the topical composition further comprises a selectininhibitor selected from the group consisting of nordihydroguaiaretic acid, a sialylated or sulfated fucooligosaccharide, a leumedin, a 3-carboxyaralkyl-substituted 2-α-D-mannopyranosyloxy-phenyl alkane being unsubstituted, oxygen-substituted, or nitrogen-substituted, or a triterpene glucoside.

13. The method of claim 12, wherein the triterpene glucoside is glycyrrhizin.

14. The method of claim 5, wherein the AP-1 inhibitor is a retinoid.

* * * * *